United States Patent [19]

Barker et al.

[11] 4,155,813

[45] May 22, 1979

[54] FERMENTATION PROCESS

[75] Inventors: Sidney A. Barker; Roderick N. Greenshields, both of Birmingham, England; John D. Humphreys, Miami, Fla.; John F. Kennedy, Birmingham, England

[73] Assignee: Gist-Brocades N.V., Delft, Netherlands

[21] Appl. No.: 768,486

[22] Filed: Feb. 14, 1977

[30] Foreign Application Priority Data

Feb. 20, 1976 [GB] United Kingdom ................ 6841/76

[51] Int. Cl.$^2$ ............................ C12J 1/04; C12B 1/20; C12D 1/02
[52] U.S. Cl. ........................................ 195/49; 195/59; 195/65; 195/DIG. 11; 426/17
[58] Field of Search ....................... 195/47, 49, 65, 52, 195/59, 57, 114, 115, 116, DIG. 11; 426/7, 17

[56] References Cited

U.S. PATENT DOCUMENTS

| | | | |
|---|---|---|---|
| 1,948,836 | 2/1934 | Ash | 195/116 X |
| 2,020,251 | 11/1935 | Stiles | 195/116 X |
| 2,717,852 | 9/1955 | Stone | 195/116 X |
| 3,912,593 | 10/1975 | Barker et al. | 195/57 |

OTHER PUBLICATIONS

Barker et al., "Enzyme Reactors for Industry," *Process Biochemistry,* vol. 6, No. 10, (Oct. 1971) pp. 11-13.

*Primary Examiner*—Thomas G. Wiseman
*Attorney, Agent, or Firm*—Hammond & Littell

[57] ABSTRACT

Fermentation process, e.g. for the production of an oxidation product such as vinegar, which comprises continuously cultivating a bacterial strain, preferably in a vessel of elongated shape, in a medium containing the substrate to be fermented in the presence of a hydrous oxide of a metal selected from the group consisting of titanium, vanadium, zirconium, iron and tin and a chelated polyhydroxy support. The bacterial strain used in the process is preferably chelated or complexed with the hydrous metal oxide and the polyhydroxy support.

15 Claims, No Drawings

FERMENTATION PROCESS

STATE OF THE ART

Vinegar production is an important fermentation process in which vinegar is produced from dilute aqueous alcoholic solutions such as charging wort. Vinegar is made by a variety of processes and the most widely used modern apparatus for the production of vinegar is the Fring's generator (British Pat. No. 731,804 and No. 1,101,560) which is a semi-continuously operated, vortex-stirred tank giving volumetric efficiencies of up to 0.5 (the volumetric efficiency is the ratio between the volume produced daily and the effective volume of the fermentation vessel) with 96 to 98% conversion of ethanol into acetic acid, thus permitting performances of up to 0.48 to 0.49 (the performance is obtained by multiplying the volumetric efficiency and the percentage of conversion divided by a factor 100). This system has still not entirely replaced the much older and far less efficient, so-called "Quick" process (cf. British Pat. No. 781,584), involving the continuous recirculation and sparging over birch twigs and other fillings in large wooden vats.

A recent development in the production of vinegar is that of Greenshields (cf. British Pat. No. 1,263,059), using an elongated vessel similar to that of the Fring's generator, but using an upwardly moving fermentation medium, whereas the Fring's process uses a downward stream. According to the Greenshields process, volumetric efficiencies of up to about 1.0 are achieved, with up to 88% conversion, thus permitting a performance of about 0.88.

In the vinegar process special kinds of bacteria are used, generally Acetobacter species, and for a high efficiency it is advantageous that the bacteria are well suspended in the culture medium. On the other hand, it is preferable that the bacteria settle quickly to achieve high volumetric efficiencies without the risk that the bacteria, or a substantial part thereof, are taken along with the final product, in which they remain suspended. Therefore, it is important to use elongated vessels, as indicated in British Pat. No. 1,263,059. Loss of bacteria can also be reduced by including a separate sedimentation vessel having a larger cross-section than the fermentation vessel to achieve sedimentation of the bacteria. Thus, an important limitation of the volumetric efficiency of known processes is the limited capability of the bacteria to settle out before removal of the final product.

To achieve a higher volumetric efficiency, it could be considered desirable to use a flocculant strain of bacterium, as for example is known for yeast (cf. for example Greenshields and Smith, The Chemical Engineer, May 1971, pages 182-190). Unfortunately, however, bacteria are generally not flocculant but, as indicated in U.S. Pat. No. 3,912,593, cells of *Escherichia coli* and yeast can be immobilized by certain hydrous metal oxides, i.e. hydrous metal oxides of Ti, V, Fe, Zr and Sn and it was shown in the said patent that *E. Coli* cells immobilized with hydrous zirconium oxide at pH 7 still respired.

OBJECTS OF THE INVENTION

It is an object of the invention to provide a novel continuous fermentation process in a medium containing a hydrous oxide of titanium, vanadium, zirconium, iron or tin and a chelated polyhydroxy support.

It is a further object of the invention to provide a continuous fermentation process with a bacterial strain chelated or complexed with a hydrous metal oxide and a polyhydroxy support.

It is an additional object of the invention to provide a novel chelate of a polyhydroxy support and a hydrous oxide of a metal selected from the group consisting of titanium, vanadium, zirconium, iron and tin.

These and other objects and advantages of the invention will become obvious from the following detailed description.

THE INVENTION

The novel fermentation process of the invention comprises continuously cultivating a bacterial strain, preferably in a vessel of elongated shape, in a medium containing the substrate to be fermented in the presence of a hydrous oxide of a metal selected from the group consisting of titanium, vanadium, zirconium, iron and tin and a chelated polyhydroxy support.

We have found surprisingly that bacteria cells, like Serratia marcescens could grow out of the previously immobilized cells obtained by addition of a hydrous metal oxide (e.g. the hydrous oxides of zirconium and titanium). On close examination, it was found that the above hydrous metal oxides formed a wide spectrum of metal chelates with bacterial cells and the most effective hydrous metal oxide at the lowest pH range was hydrous titanium oxide, which was quite effective at around pH 3. Therefore, it was chosen to assess if it could cause aggregation and subsequent flocculation of Acetobacter cells during vinegar production. The object was to increase the rate of production of the oxidation product, i.e. acetic acid, within the one continuously operated fermenter. Hopefully, it would effect this by aggregation and flocculation of the cells, thus permitting increased flow-rates without excessive wash-out of the bacteria in the fermenter.

Such increased flow-rates were achieved but by themselves would not necessarily have increased the rate of production. The increased flow rate could have been accompanied by a reduction in the conversion of ethanol to acetic acid. Surprisingly, the sum total of catalytic activity of the cells was retained and even increased at the increased flow-rates probably by the retention of increased numbers of cells within the fermenter which, when aggregated and flocculated together, had the same or even an increased catalytic surface still accessible to substrate.

When carrying out these experiments it appeared, however, that only some kinds of Acetobacter showed a positively increased performance in the continuously operated fermenter, especially Acetobacter derived from the above-indicated "Quick" process, whereas other species, particularly those currently found in industrially operated tower fermenters, did not.

Surprisingly it has been found, according to the invention, that for the effective chelation of some strains of Acetobacter with hydrous metal oxides, e.g. hydrous titanium oxide, another component to which the hydrous metal oxide should be chelated should be present, i.e. a polyhydroxy support such as cellulose. Some kinds of Acetobacter, especially those used in the "Quick" process such as Acetobacter xylinum, produce extracellular cellulose by themselves, whereas others, especially those used in industrial tower fermenters, do not so that a hydrous metal chelated polyhydroxy support such as hydrous titanium oxide chelated cellulose should be added in the latter case to achieve effective immobilization of the bacteria. Also in other fermentation processes, such as the oxidation of glucose to 5-glucono-lactone and gluconic acid by Pseudomonas, use can be made of this technique.

The present invention accordingly provides a fermentation process which comprises continuously cultivating a bacterial strain, preferably in a vessel of elongated shape, in a medium containing the substrate to be fermented in the presence of a hydrous oxide of titanium, vanadium, zirconium, iron or tin and a chelated polyhyroxy support. The chelated polyhydroxy support may be derived from the bacterial strain (cf. Acetobacter xylinum referred to above).

According to a feature of the present invention, a bacterial strain is provided for use in a fermentation process, chelated or complexed with a hydrous metal oxide of titanium, vanadium, zirconium, iron or tin and a polyhydroxy support chelated to the hydrous metal oxide. According to a further feature of the present invention, there is provided a hydrous metal oxide of titanium, vanadium, zirconium, iron or tin chelated with a polyhydroxy support suitable for use in the fermentation process of the invention. Performances of up to about twice those of known processes for producing vinegar may be achieved by the invention. If the bacterial strain does not produce the polyhydroxy support by itself, a sufficient amount of that compound, chelated to the hydrous metal oxide, should be added to the fermentation medium. The polyhydroxy support is preferably cellulose, and the preferred hydrous oxide is that of tetravalent titanium.

The hydrous metal oxide and the polyhydroxy support are not effective if added to the fermentation medium separately (if a non-aggregating bacterium strain is used) and it is desirable to chelate the hydrous metal oxide to the polyhydroxy support before addition to the fermentation medium.

In a further feature of the invention, the hydrous metal oxide-chelated polyhydroxy support is prepared by contacting a hydrolyzable compound of titanium, vanadium, zirconium, iron or tin, optionally in solution, with the polyhydroxy support, optionally drying the mixture obtained and subsequently washing the mixture with water. This may be done, for example, by mixing cellulose powder and titanium tetrachloride in solution, drying the mixture and washing the dried mixture with distilled water until the washings are neutral. The hydrous metal oxide-chelated polyhyroxy support thus obtained should not be heat-dried prior to use.

The titanium tetrachloride used in the procedure described above may be replaced by other hydrolyzable metal compounds, for example titanium lactose, titanium citrate, titanium urea or titanium acrylamide. The pH at which the polyhydroxy support is initially treated with the titanium compound will vary with the particular compound used. The metal compound should be substantially non-hydrolyzed before contact with the polyhydroxy support.

An aqueous solution of the metal compound may be used if the pH of the solution is adjusted substantially to prevent hydrolysis. Alternatively, a solution of the metal compound in an organic solvent may be used. The organic solvent must then be removed prior to addition of the hydrous metal oxide-chelated polyhydroxy support to the fermentation medium.

When a hydrous metal oxide is used with a bacterium strain which produces its own polyhydroxy support, the hydrous metal oxide may be formed in situ by the addition to the fermentation medium of a metal compound hydrolyzable at the pH of the fermentation medium, e.g. titanium chelated lactose, titanium citrate or titanium urea. The use of titanium acrylamide to produce hydrous titanium oxide in situ for a food product fermentation would be undesirable. It will be appreciated that the hydrolyzable metal compound, e.g. titanium chelated lactose, used to produced hydrous metal oxide in situ does not have to be non-biodegradable at the pH of the medium.

Other chelates in which hydrous titanium oxide is chelated to a polyhydroxy support which are suitable for use in the process of the invention and made in an analogous manner to the hydrous titanium-cellulose chelate include those based on wood, sawdust, water-insoluble polysaccharides, cross-linked polysaccharides, glass, siliaceous materials such as Celite and Neosyl, in addition to a wide range of polymers containing C—OH groups or Si—OH groups in the form of powders, beads or fibers.

The polyhydroxy support must form with the hydrous metal oxide a chelate which is substantially insoluble, non-hydrolyzable and non-biodegradable in the fermentation medium at the pH, temperature and ionic concentration employed. The disposition of hydroxy groups on the polyhyroxy support must be such to permit chelation with the metal. The polyhydroxy support itself need not be water insoluble. If the pH varies during the fermentation, the chelate must be insoluble during part of the fermentaion, preferably the part associated with maximum production of the desired fermentation product.

Different hydrous metal oxides and hydrous metal oxide-chelated polyhydroxy supports will chelate or complex with the bacteria used in a fermentation process to an extent which will vary with the pH of the medium.

When a hydrous metal oxide alone is used in the fermentation process of the invention, the amount of hydrous metal oxide used is suitably from about 0.01 to about 2.2 g/liter of fermentation fluid per day. When a hydrous metal oxide-chelated polyhyroxy support is used, the ratio of hydrous metal oxide (expressed in terms of metal) to polyhydroxy support is preferably about 1:2 to about 1:25 (w/w), the amount of hydrous metal oxide (expressed in terms of metal) preferably being from about 0.02 to about 2.0 g/liter of fermentation fluid per day, the preferred amount of polyhydroxy support being from about 0.045 to about 4.5 g/liter of fermentation fluid per day.

The invention is particularly advantageous for the production of a food product such as vinegar since although titanium dioxide is considered non-toxic and (in several countries) a permitted food additive, the average level remaining after filtration through Kieselguhr is only 5 ppm at most.

Although the invention is preferably carried out in a fermenter such as described in British Pat. No. 1,263,059, it is also possible to use, for example, Fring's generator for carrying out the invention.

In any of the fermentations of the invention, the substrate giving rise to an oxidation product need not be the immediate precursor of the oxidation product, but could be a metabolic precursor several steps removed from the oxidation product, e.g. glucose or sucrose for lactic acid production. Further, although the fermentations are preferably those taking place in the presence of a gas containing oxygen such as air, the oxidation product need not arise by actual reaction of the substrate or its metabolite with oxygen, but can arise by some other oxidation process. Furthermore, the invention can be used in non-oxidative fermentations such as the fermentation of glucose to e.g. butylene glycol.

The addition of hydrous metal oxide or hydrous metal-polyhydroxy support confers further unforeseen advantages on the fermentation, for example (a) it confers greater resistance to disturbance by frothing so that, where desired, greater aeration rates can be employed. Where oxygen is a direct participant in the reaction as in the conversion of ethanol to acetic acid, this is particularly advantageous; (b) better consistency of the production can be attained in the presence of the additive since in addition to (a) it becomes less sensitive to wash-out.

In the following examples there are described several preferred embodiments to illustrate the invention. However, it should be understood that the invention is not intended to be limited to the specific embodiments.

EXAMPLE 1A

Hydrous titanium oxide

To given amounts of titanium tetrachloride (present as 15% w/v solution in 15% w/v hydrochloric acid), there was added 2N ammonium hydroxide solution with stirring to precipitate the hydrous titanium oxide and to obtain a pH equal to that in the fermenter (approximately pH 3.0). The suspension of hydrous titanium oxide was diluted to about 100 ml with distilled water, was stirred vigorously and was added to the fermenter contents. Mixing was accomplished very rapidly (10 to 20 sec) by the efficient aeration pattern.

EXAMPLE 1B

Hydrous titanium-cellulose chelate 1.2 g of chromatographic cellulose powder (Whatman CF 11) and 1.2 g of titanium tetrachloride (in solution, as above) were mixed and stirred for 2 hours. The mixture was then dried at 45° C., ground to a powder, washed with distilled water until the washings were neutral to pH indicator paper and then added to the fermenter as an aqueous suspension.

EXAMPLE 1

Production of malt vinegar by a non-aggregating strain of Acetobacter in the presence of titanium-chelated cellulose A glass tower fermenter of a cylindrical shape was used which had a high aspect ratio (height to diameter ratio) containing microorganisms suspended in the medium and through which there is a uni-directional flow of medium and/or gases. The fermenter used in this experiment had a volume of 2.6 liters, a height of 57 cm and an average diameter of 7.32 cm so that its aspect ratio was 7.8:1. In operating the fermenter, compressed air was passed through a pressure regulator and filter, then through a flowmeter to measure its flow rate and finally into the fermenter medium via a sintered glass disc fused into the base of the fermenter.

The effluent air from the fermenter was passed through two water-cooled (4° C.) condensers to ensure that any volatile components in it was returned to the bulk of the liquid. The temperature of the fermenter was maintained at 32° C. by a water jacket surrounding the fermenter which was fed by thermostatically controlled water. The rate of medium flow in the fermenter was controlled by a variable speed peristaltic pump and the flow rate through the fermenter was measured by collecting the vinegar produced over a period of approximately 24 hours and expressed as volumetric efficiency (V.E.) defined as $$\frac{\text{flow rate per day}}{\text{fermenter volume}}.$$

The medium used in the experiments is known commercially as "charging wort" and is a dilute aqueous ethanol solution containing about 6% w/v of ethanol and is produced by a process similar to that used for beer and spirit fermentation from malted barley wort. In this experiment, a culture of a non-aggregating strain of Acetobacter was used which was obtained from a tower fermenter of a commercial malt vinegar manufacture and was known not to aggregate or produce extra-cellular polysaccharide material.

At the beginning of each experiment, the fermenter was half-filled with charging wort, an inoculum (50-100 ml) of the culture was added and aeration was commenced at a low rate (0.1 to 0.2 v/v/m=volumes air/fermenter volume/minute). Samples were taken at intervals and tested for acetic acid and ethanol content. When the acidity reached about 4% w/v, the peristaltic pump was turned on and the medium was metered into the fermenter. The fermentation was then allowed to proceed continuously with the medium flow rate and aeration rate being manipulated to maximize the acetic acid content of the fermenter (7% w/v approximately) and minimize ethanol content (less than 0.57%). Measurements of pH, optical density (600 nm) and titanium content (if present) were also made.

The fermentation was started without addition of the titanium hydroxide or the chelated titanium-cellulose complex. Addition of hydrous titanium hydroxide was started only after the fermenter operated continuously at optimal conditions of medium flow rate and aeration for several consecutive days. Some typical results are given below:

| Number of consecutive days | Average aeration (v/v/m) | Hydrous titanium oxide added daily | | Performance |
| --- | --- | --- | --- | --- |
| | | Ti (g) | cellulose (g) | |
| 2 | 0.58 | — | — | 0.95 |
| 2 | 0.58 | 0.26 | — | 1.00 |
| 2 | 0.57 | 0.53 | — | 1.08 |
| 2 | 0.63 | 0.53 | 1.2 | 1.47 |
| 2 | 0.79 | 0.53 | 1.2 | 1.44 |

The table shows that the addition of hydrous titanium oxide, either from 0.26 g. Ti or from 0.53 g. Ti does hardly improve the performance of the tower fermenter, but that a marked increase of the performance is achieved after the addition of the hydrous titanium-cellulose chelate (expressed in the table in terms of its equivalent hydrous titanium oxide and cellulose content).

EXAMPLE 2

An 8 liter tower fermenter (aspect ratio 14:1) was constructed and continuous production of acetic acid initiated in a manner similar to and under the conditions of Example 1 using the non-aggregating strain of Acetobacter. After a period of time during which the optimum operating parameters and highest operating efficiencies were established, additions of hydrous titanium oxide and subsequently a mixture of hydrous titanium oxide and cellulose powder (Whatman CF 11) were made. The results of these additions are given below:

| Number of consecutive days | Average aeration (v/v/m) | Hydrous titanium oxide added daily (Ti g) | Cellulose added daily (g) | Performance |
|---|---|---|---|---|
| 2 | 1.10 | — | — | 1.23 |
| 2 | 1.12 | 0.51 | — | 1.24 |
| 2 | 0.45 | 1.52 | — | 1.22 |
| 2 | 0.43 | 1.52 | 6 | 0.88 |

This Example shows that the effect of Example 1 is not produced by a mere mixture of hydrous titanium oxide and cellulose and, in fact, this mixture is even somewhat deleterious to the process. Only the titanium-cellulose combinations in which the titanium oxide is chelated to the cellulose works with the non-aggregating species.

EXAMPLE 3

Production of malt vinegar by a polysaccharide producing species of Acetobacter in the presence of hydrous titanium oxide The experiment was carried out in the fermenter of Example 2 and an aggregating strain of Acetobacter capable of producing polysaccharide which was obtained from a commercial malt vinegar manufacturer employing the "Quick" process in which such strains predominate was used. After a period of time in which the highest level at which the fermenter would operate was established, hydrous titanium oxide was added to the fermenter and the results obtained after this treatment, compared with those before, are as below:

| Number of consecutive days | Average aeration (v/v/m) | Hydrous titanium oxide added daily Ti (g) | cellulose (g) | Volumetric efficiency (V.E.) | Percentage conversion | Performance | Amount of Ti in solution (ppm) Fermenter | Effluent |
|---|---|---|---|---|---|---|---|---|
| 2 | 0.50 | — | — | 0.77 | 82 | 0.63 | — | — |
| 5 | 1.50 | 0.32 | — | 1.49 | 91 | 1.36 | 1.8 | 2.1 |
| 5 | 1.50 | 0.32 | — | 1.79 | 94 | 1.68 | | |

| Number of consecutive days | Average aeration (v/v/m) | Hydrous titanium oxide added daily Ti (g) | Performance |
|---|---|---|---|
| 2 | 0.31 | — | 1.10 |
| 2 | 0.31 | — | 1.10 |
| 8 | 0.31 | — | 1.08 |
| 8 | 0.39 | 1.76 | 1.50 |

The table shows that addition of hydrous titanium oxide alone, i.e. not chelated to a polyhydroxy support, is sufficient to show a marked increase of the performance when an aggregating strain of Acetobacter is used.

EXAMPLE 4

Production of malt vinegar by a polysaccharide producing species of Acetobacter in the presence of hydrous titanium oxide.

The 2.6 liter tower fermenter of Example 1 was prepared for the continuous production of malt vinegar as in that Example and then the fermenter was inoculated with the aggregating species of Acetobacter capable of producing polysaccharide from the "Quick" process with the fermentation allowed to run for 29 days before addition of hydrous titanium oxide was commenced. Additions were continued over a long period of time (about 50 days) during which time the volumetric efficiency of the fermenter was slowly increased. Some of the results of this treatment are given below.

| Number of consecutive days | Average aeration (v/v/m) | Hydrous titanium oxide added daily Ti (g) | Performance |
|---|---|---|---|
| 2 | 0.49 | — | 0.63 |
| 2 | 1.50 | 0.33 | 1.48 |
| 2 | 1.50 | 0.33 | 1.53 |

Example 4 illustrates that increase in operating performance is not limited to just one fermenter. In an experiment almost identical to that of Example 3, very similar results were obtained by the addition of hydrous titanium oxide to an aggregating species of Acetobacter.

EXAMPLE 5

Production of malt vinegar by a polysaccharide producing species of Acetobacter in the presence of hydrous titanium oxide In this experiment, the tower fermenter of Example 1 was used and the vinegar production was carried out with the aggregating species of Acetobacter of Examples 3 and 4. The flow rate of the medium was controlled to attempt to keep the conversion of ethanol to acetic acid above about 90%. Samples were taken from the fermenter and from the effluent receiver and assayed for dissolved titanium colorimetrically at 600 nm. The results were as follows:

The table shows again that an important increase in performance is achieved after the addition of hydrous titanium oxide to an aggregating strain of Acetobacter. The table shows further that the amounts of titanium in solution in the fermenter and in the effluent are extemely low.

EXAMPLE 6

Production of malt vinegar by a non-aggregating species of Acetobacter in the presence of titanium chelated cellulose In this Example, the fermenter of Example 1 was used as well as the non-aggregating strain of Acetobacter of Example 1 and additions of hydrous titanium oxide and titanium-chelated cellulose were studied. The results are shown in the following table:

| Number of consecutive days | Average aeration (v/v/m) | Hydrous titanium oxide added daily | | Volumetric efficiency (V.E.) | Conversion % | Performance |
|---|---|---|---|---|---|---|
| | | Ti (g) | cellulose (g) | | | |
| 5 | 0.58 | — | — | 1.15 | 91 | 1.04 |
| 3 | 0.58 | 0.26 | — | 1.14 | 86 | 0.99 |
| 5 | 0.69 | 0.53 | — | 1.18 | 88 | 1.05 |
| 5 | 0.85 | 0.53 | 1.2 | 1.63 | 80 | 1.30 |

As in Example 1, the table shows that the addition of hydrous titanium oxide alone, i.e. not chelated to cellulose, is insufficient to provoke a significant increase of the performance, but after addition of the hydrous titanium-cellulose chelate, a marked increase of the performance is shown.

Various modifications of the process and products of the invention may be made without departing from the spirit or scope thereof and it is to be understood that the invention is to be limited only as defined in the appended claims.

We claim:

1. A fermentation process comprising continuously cultivating a non-extracellular cellulose producing or extracellular cellulose producing bacterial strain in a medium containing the substrate to be fermented in the presence of about 0.01 to about 2.2 grams per liter hydrous oxide of a metal selected from the group consisting of titanium, vanadium, zirconium, iron and tin, chelated to a polyhydroxy support selected from the group consisting of cellulose, wood, saw dust, glass, siliaceous materials and polymers containing C—OH or Si—OH groups wherein, when the bacterial strain is a non-extracellular cellulose producing strain, the metal oxide polyhydroxy support chelate has a weight ratio of hydrous metal oxide (expressed in terms of metal) to polyhydroxy support of about 1:2 to about 1:25 (w/w) and is added to the medium and when the bacterial strain is an extracellular cellulose producing strain, the metal oxide polyhydroxy support chelate is formed in situ in the medium from the hydrous metal oxide the cellulose produced extracellularly by the strain.

2. A process of claim 1 wherein the cultivation is effected in an elongated vessel.

3. A process of claim 1 wherein the chelated polyhydroxy support is a polymer containing C—OH groups or Si—OH groups capable of forming with the hydrous metal oxide a chelate which is substantially insoluble, non-hydrolyzable and non-biodegradable in the fermentation medium at the pH, the temperature and the ionic concentration employed.

4. A process of claim 3 wherein the polyhydroxy support is cellulose produced by the extracellular cellulose producing strain.

5. A process of claim 4 wherein the hydrous metal oxide is formed in situ by addition to the fermentation medium of a metal compound hydrolyzable at the pH of the fermentation medium to form the hydrous metal oxide.

6. A process of claim 5 wherein the metal compound is selected from the group consisting of titanium chelated lactose, titanium citrate and titanium urea.

7. A process of claim 4 wherein the amount of hydrous metal oxide (expressed in terms of metal) is from about 0.02 to about 2.0 g/liter of medium per day.

8. A process of claim 1 wherein the hydrous metal oxide is chelated to the polyhydroxy support before addition to the fermentation meium.

9. A process of claim 8 wherein the hydrous metal oxide-chelated polyhydroxy support is prepared by contacting a hydrolyzable compound of a metal selected from the group consisting of titanium, vanadium, zirconium, iron and tin, with the polyhydroxy support and subsequently washing the mixture with water.

10. A process of claim 9 wherein the hydrolyzable compound of titanium is selected from the group consisting of titanium tetrachloride, titanium lactose, titanium citrate, titanium urea and titanium acrylamide.

11. A process of claim 9 wherein the hydrolyzable compound of titanium is titanium tetrachloride.

12. A process of claim 8 wherein the polyhydroxy support is selected from the group consisting of cellulose, wood, saw dust, water-insoluble polysaccharide, cross-linked polysaccharide and glass.

13. A process of claim 8 wherein the polyhydroxy support is cellulose.

14. A process of claim 1 for the preparation of vinegar wherein the bacterium employed is an Acetobacter strain.

15. A process of claim 14 wherein the bacterium is *Acetobacter xylinum*.

* * * * *